(12) United States Patent
Namiranian et al.

(10) Patent No.: US 10,080,627 B2
(45) Date of Patent: *Sep. 25, 2018

(54) ORTHODONTIC TOOTH MOVEMENT DEVICE, SYSTEMS AND METHODS

(71) Applicant: Align Technology, Inc., San Jose, CA (US)

(72) Inventors: Parshan Namiranian, San Jose, CA (US); Ali Kakavand, San Carlos, CA (US); Eric Kuo, Foster City, CA (US)

(73) Assignee: Align Technology, Inc., San Jose, CA (US)

(*) Notice: Subject to any disclaimer, the term of this patent is extended or adjusted under 35 U.S.C. 154(b) by 296 days.

This patent is subject to a terminal disclaimer.

(21) Appl. No.: 14/801,507

(22) Filed: Jul. 16, 2015

(65) Prior Publication Data

US 2015/0320518 A1 Nov. 12, 2015

Related U.S. Application Data

(63) Continuation of application No. 12/126,714, filed on May 23, 2008, now Pat. No. 9,119,691.

(51) Int. Cl.
| | | |
|---|---|---|
| *A61C 3/00* | (2006.01) | |
| *A61C 7/10* | (2006.01) | |
| *A61C 7/08* | (2006.01) | |

(52) U.S. Cl.
CPC . *A61C 7/10* (2013.01); *A61C 7/08* (2013.01)

(58) Field of Classification Search
CPC .................................. A61C 7/00; A61C 7/08
USPC .............. 433/3, 6, 18–19, 21, 24, 37, 41–48
See application file for complete search history.

(56) References Cited

U.S. PATENT DOCUMENTS

| | | | |
|---|---|---|---|
| 2,467,432 A | 4/1949 | Kesling | |
| 3,407,500 A | 10/1968 | Kesling | |
| 3,600,808 A | 8/1971 | Reeve | |
| 3,660,900 A | 5/1972 | Andrews | |
| 3,683,502 A | 8/1972 | Wallshein | |
| 3,738,005 A | 6/1973 | Cohen | |

(Continued)

FOREIGN PATENT DOCUMENTS

| | | | |
|---|---|---|---|
| AU | 3031677 A | 5/1979 | |
| AU | 517102 B2 | 7/1981 | |

(Continued)

OTHER PUBLICATIONS

AADR. American Association for Dental Research, Summary of Activities, Mar. 20-23, 1980, Los ngeles, CA, p. 195.

(Continued)

*Primary Examiner* — Matthew Nelson
(74) *Attorney, Agent, or Firm* — Wilson Sonsini Goodrich & Rosati (57) ABSTRACT

The present invention provides orthodontic appliances and systems, and related methods, for applying a force to a target tooth as an appliances is worn by the patient. One positioning appliance includes a tooth positioning appliance having teeth receiving cavities shaped to apply a positioning force to the patient's teeth. The appliance includes a spring-loaded tooth movement device disposed in the appliance so as to engage an attachment mounted on a surface of a patient's tooth and apply a force to the tooth.

20 Claims, 7 Drawing Sheets

(56) References Cited

U.S. PATENT DOCUMENTS

| | | | |
|---|---|---|---|
| 3,837,081 A * | 9/1974 | Kesling | A61C 7/08 433/6 |
| 3,860,803 A | 1/1975 | Levine | |
| 3,916,526 A | 11/1975 | Schudy | |
| 3,922,786 A | 12/1975 | Lavin | |
| 3,950,851 A | 4/1976 | Bergersen | |
| 3,983,628 A | 10/1976 | Acevedo | |
| 4,014,096 A | 3/1977 | Dellinger | |
| 4,195,046 A | 3/1980 | Kesling | |
| 4,253,828 A | 3/1981 | Coles et al. | |
| 4,324,546 A | 4/1982 | Heitlinger et al. | |
| 4,324,547 A | 4/1982 | Arcan et al. | |
| 4,348,178 A | 9/1982 | Kurz | |
| 4,478,580 A | 10/1984 | Barrut | |
| 4,500,294 A | 2/1985 | Lewis | |
| 4,504,225 A | 3/1985 | Yoshii | |
| 4,505,673 A | 3/1985 | Yoshii | |
| 4,526,540 A | 7/1985 | Dellinger | |
| 4,575,330 A | 3/1986 | Hull | |
| 4,575,805 A | 3/1986 | Moermann et al. | |
| 4,591,341 A | 5/1986 | Andrews | |
| 4,609,349 A | 9/1986 | Cain | |
| 4,611,288 A | 9/1986 | Duret et al. | |
| 4,656,860 A | 4/1987 | Orthuber et al. | |
| 4,663,720 A | 5/1987 | Duret et al. | |
| 4,664,626 A | 5/1987 | Kesling | |
| 4,676,747 A | 6/1987 | Kesling | |
| 4,742,464 A | 5/1988 | Duret et al. | |
| 4,755,139 A | 7/1988 | Abbatte et al. | |
| 4,763,791 A | 8/1988 | Halverson et al. | |
| 4,793,803 A * | 12/1988 | Martz | A61C 7/08 433/6 |
| 4,798,534 A | 1/1989 | Breads | |
| 4,836,778 A | 6/1989 | Baumrind et al. | |
| 4,837,732 A | 6/1989 | Brandestini et al. | |
| 4,850,864 A | 7/1989 | Diamond | |
| 4,850,865 A | 7/1989 | Napolitano | |
| 4,856,991 A | 8/1989 | Breads et al. | |
| 4,877,398 A | 10/1989 | Kesling | |
| 4,880,380 A | 11/1989 | Martz | |
| 4,889,238 A | 12/1989 | Batchelor | |
| 4,890,608 A | 1/1990 | Steer | |
| 4,935,635 A | 6/1990 | O'Harra | |
| 4,936,862 A | 6/1990 | Walker et al. | |
| 4,937,928 A | 7/1990 | van der Zel | |
| 4,941,826 A | 7/1990 | Loran et al. | |
| 4,964,770 A | 10/1990 | Steinbichler et al. | |
| 4,975,052 A | 12/1990 | Spencer et al. | |
| 4,983,334 A | 1/1991 | Adell | |
| 5,011,405 A | 4/1991 | Lemchen | |
| 5,017,133 A | 5/1991 | Miura | |
| 5,027,281 A | 6/1991 | Rekow et al. | |
| 5,035,613 A | 7/1991 | Breads et al. | |
| 5,055,039 A | 10/1991 | Abbatte et al. | |
| 5,059,118 A | 10/1991 | Breads et al. | |
| 5,100,316 A | 3/1992 | Wildman | |
| 5,121,333 A | 6/1992 | Riley et al. | |
| 5,125,832 A | 6/1992 | Kesling | |
| 5,128,870 A | 7/1992 | Erdman et al. | |
| 5,130,064 A | 7/1992 | Smalley | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,145,364 A * | 9/1992 | Martz | A61C 7/00 433/18 |
| 5,176,517 A | 1/1993 | Truax | |
| 5,184,306 A | 2/1993 | Erdman et al. | |
| 5,186,623 A | 2/1993 | Breads et al. | |
| 5,257,203 A | 10/1993 | Riley et al. | |
| 5,273,429 A | 12/1993 | Rekow et al. | |
| 5,278,756 A | 1/1994 | Lemchen et al. | |
| 5,328,362 A | 7/1994 | Watson et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,440,326 A | 8/1995 | Quinn | |
| 5,440,496 A | 8/1995 | Andersson et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,431,562 A | 11/1995 | Andreiko et al. | |
| 5,474,448 A | 12/1995 | Andreiko et al. | |
| RE35,169 E | 3/1996 | Lemchen et al. | |
| 5,518,397 A | 5/1996 | Andreiko et al. | |
| 5,528,735 A | 6/1996 | Strasnick et al. | |
| 5,533,895 A | 7/1996 | Andreiko et al. | |
| 5,542,842 A | 8/1996 | Andreiko et al. | |
| 5,549,476 A | 8/1996 | Stern | |
| 5,562,448 A | 10/1996 | Mushabac | |
| 5,587,912 A | 12/1996 | Andersson et al. | |
| 5,605,459 A | 2/1997 | Kuroda et al. | |
| 5,607,305 A | 3/1997 | Andersson et al. | |
| 5,614,075 A | 3/1997 | Andre | |
| 5,621,648 A | 4/1997 | Crump | |
| 5,645,420 A | 7/1997 | Bergersen | |
| 5,645,421 A | 7/1997 | Slootsky | |
| 5,655,653 A | 8/1997 | Chester | |
| 5,683,243 A | 11/1997 | Andreiko et al. | |
| 5,692,894 A | 12/1997 | Schwartz et al. | |
| 5,725,376 A | 3/1998 | Poirier | |
| 5,725,378 A | 3/1998 | Wang | |
| 5,733,126 A | 3/1998 | Andersson et al. | |
| 5,740,267 A | 4/1998 | Echerer et al. | |
| 5,742,700 A | 4/1998 | Yoon et al. | |
| 5,799,100 A | 8/1998 | Clarke et al. | |
| 5,800,174 A | 9/1998 | Andersson | |
| 5,823,778 A | 10/1998 | Schmitt | |
| 5,848,115 A | 12/1998 | Little et al. | |
| 5,857,853 A | 1/1999 | van Nifterick et al. | |
| 5,866,058 A | 2/1999 | Batchelder et al. | |
| 5,879,158 A | 3/1999 | Doyle et al. | |
| 5,880,961 A | 3/1999 | Crump | |
| 5,880,962 A | 3/1999 | Andersson et al. | |
| 5,934,288 A | 8/1999 | Avila et al. | |
| 5,957,686 A | 9/1999 | Anthony | |
| 5,964,587 A | 10/1999 | Sato | |
| 5,971,754 A | 10/1999 | Sondhi et al. | |
| 5,975,893 A | 11/1999 | Chishti et al. | |
| 6,015,289 A | 1/2000 | Andreiko et al. | |
| 6,044,309 A | 3/2000 | Honda | |
| 6,049,743 A | 4/2000 | Baba | |
| 6,062,861 A | 5/2000 | Andersson | |
| 6,068,482 A | 5/2000 | Snow | |
| 6,099,314 A | 8/2000 | Kopelman et al. | |
| 6,123,544 A | 9/2000 | Cleary | |
| 6,152,731 A | 11/2000 | Jordon et al. | |
| 6,183,248 B1 | 2/2001 | Chishti et al. | |
| 6,190,165 B1 | 2/2001 | Andreiko et al. | |
| 6,217,325 B1 | 4/2001 | Chishti et al. | |
| 6,217,334 B1 | 4/2001 | Hultgren | |
| 6,244,861 B1 | 6/2001 | Andreiko et al. | |
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,402,707 B1 | 6/2002 | Ernst | |
| 6,482,298 B1 | 11/2002 | Bhatnagar | |
| 6,524,101 B1 | 2/2003 | Phan et al. | |
| 6,554,611 B2 | 4/2003 | Chishti et al. | |
| 6,572,372 B1 | 6/2003 | Phan et al. | |
| 6,629,840 B2 | 10/2003 | Chishti et al. | |
| 6,705,863 B2 | 3/2004 | Phan et al. | |
| 6,722,880 B2 | 4/2004 | Chishti et al. | |
| 9,119,691 B2 | 9/2015 | Namiranian et al. | |
| 2002/0006597 A1 | 1/2002 | Andreiko et al. | |
| 2003/0009252 A1 | 1/2003 | Pavlovskaia et al. | |
| 2003/0139834 A1 | 7/2003 | Nikolskiy et al. | |

(56) References Cited

U.S. PATENT DOCUMENTS

| | | | |
|---|---|---|---|
| 2003/0190576 A1* | 10/2003 | Phan | A61C 7/00 433/6 |
| 2003/0224311 A1 | 12/2003 | Cronauer | |
| 2004/0128010 A1 | 7/2004 | Pavlovskaia et al. | |
| 2004/0170941 A1* | 9/2004 | Phan | A61C 7/00 433/6 |
| 2004/0219471 A1* | 11/2004 | Cleary | A61C 7/146 433/3 |
| 2005/0055118 A1 | 3/2005 | Nikolskiy et al. | |
| 2005/0064358 A1* | 3/2005 | Nicozisis | A61C 7/02 433/3 |
| 2005/0106525 A1* | 5/2005 | Knopp | A61C 7/00 433/6 |
| 2007/0065768 A1* | 3/2007 | Nadav | A61C 7/006 433/6 |
| 2009/0291406 A1 | 11/2009 | Namiranian et al. | |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging q Applications for Automated Industrial Inspection and Assembly, vol. 182, p. 187-191 (1979).
Altschuler, "3D Mapping of Maxillo-Facial Prosthesis," AADR Abstract #607, 2 pages total, (1980).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive,Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.

(56) References Cited

OTHER PUBLICATIONS

Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et al., "Three-Dimensional Computer-Assisted Design of Craniofacial Surgical Procedures: Optimization and Interaction with Cephalometric and CT—Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992).
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (1992).
DENT-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret, "Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).

Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-268 (Apr. 1989).
Heaven et al. "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http ://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), lnformatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, 18(3):33-41 (Jul. 1984).
Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).

(56) References Cited

OTHER PUBLICATIONS

Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy as One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al. "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice is Clear: Red, White & Blue . . . The Simple, Affordable, No-Braces Treatment, Allesee Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee Orthodontic Appliances-Pro Lab product information for patients, <http://ormco.com/aoa/appliancesservices/RWB/patients.html>, 2 pages (May 19, 2003).
The Choice is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050342, filed Jun. 20,1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Detofac. Orthop. vol. 95, No. 5 (May 1989) pp. 399-400.

(56) References Cited

OTHER PUBLICATIONS

Warunek et.al., Clinical Use of Silicone Elastomer Applicances, JCO (1989) XXIII(10):694-700.

Wells, Application of the Positioner Appliance in Orthodontic Treatment, Am. J. Orthodont. (1970) 58:351-366.

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13,1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980).

Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).

You May Be A Candidate for This Invisible No-Braces Treatment, Allesee Orthodontic Appliances-Pro Lab product information for patients, 2 pages (2002).

\* cited by examiner

ORTHODONTIC TOOTH MOVEMENT DEVICE, SYSTEMS AND METHODS

CROSS-REFERENCE

This application is a continuation of U.S. application Ser. No. 12/126,714, filed May 23, 2008, now U.S. Pat. No. 9,119,691, the contents of which are hereby incorporated by reference in their entirety.

BACKGROUND OF THE INVENTION

The present invention relates generally to the field of orthodontics, and more particularly to dental repositioning systems and appliances including a tooth movement device for applying a force to a tooth of a patient.

An objective of orthodontics is to move a patient's teeth to positions where function and/or aesthetics are optimized. Traditionally, appliances such as braces are applied to a patient's teeth by treating practitioner and the set of braces exerts continual force on the teeth and gradually urges them toward their intended positions. Over time and with a series of clinical visits and adjustments to the braces, the practitioner adjusts the appliances to move the teeth toward their final destination.

More recently, alternatives to conventional orthodontic treatment with traditional affixed appliances (e.g., braces) have become available. For example, systems including a series of preformed appliances/aligners have become commercially available from Align Technology, Inc., Santa Clara, Calif., under the tradename Invisalign® System. The Invisalign® System is described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "align-.com"). The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as Treat® from Align Technology, Inc. The design of the aligners can rely on computer modeling of a series of planned successive tooth arrangements, and the individual aligners are designed to be worn over the teeth and elastically reposition the teeth to each of the planned tooth arrangements.

While recently developed orthodontic treatment technologies, such as those described above, represent a considerable advancement in the field of orthodontics, additional and innovative appliance designs remain of interest. For example, in some cases certain movements such as tooth extrusion movements have shown difficult to accomplish and/or require use of various attachments and elastics. As such, improved appliances and techniques are needed for applying more effective tooth extrusion movement forces to the teeth during orthodontic treatment.

BRIEF SUMMARY OF THE INVENTION

The present invention provides improved orthodontic appliances and systems, and related methods, for more effectively applying tooth movement forces (e.g., extrusion force) and repositioning teeth in a desired arrangement. Appliances and systems of the present invention make use of an tooth movement device (e.g., spring-loaded tooth movement device) designed to apply an tooth movement force to a target tooth as an appliances is worn by the patient.

In one aspect, the present invention positioning appliances and systems include a tooth positioning appliance having teeth receiving cavities shaped to apply a positioning force to the patient's teeth. The appliance further includes a spring-loaded tooth movement device disposed in the appliance so as to engage an attachment mounted on a surface of a patient's tooth and apply tooth movement force to the tooth.

In another aspect, systems and methods of the present invention can include an attachment assembly mountable on a surface of a tooth, with the attachment assembly including a spring-loaded device. An orthodontic appliance designed to engage the attachment assembly will be provided, and can include a cavity having a relief disposed therein and shaped to receive the spring-loaded device of the attachment assembly. As the appliance is worn by the patient, the attachment assembly with the spring-loaded device coupled with the appliance can function to apply a tooth movement force to the tooth.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

The present invention relates to orthodontic positioning of teeth of a patient. Devices and systems, as well as related methods, are described for applying a tooth movement force to a patient's tooth to achieve desired repositioning of the patient's teeth.

Thus, the present invention provides tooth positioning appliances for providing orthodontic treatment to a patient. An orthodontic tooth positioning appliance of the present invention will typically be a patient-removable appliance so as to allow the patient to insert and remove the appliance from the teeth without strictly needing assistance of an orthodontic practitioner. Although, many aspects of orthodontic treatment can occur under the supervision of an orthodontic practitioner (e.g., orthodontist, dentist, etc.). An appliance can include a shell appliance (e.g., polymeric shell appliance) having teeth receiving cavities shaped to receive and apply a resilient positioning force (e.g., tooth repositioning force) to the patient's teeth. The appliance can further include tooth movement device coupled with the appliance or disposed in the appliance and designed to apply tooth movement force to a patient's tooth and elicit tooth movement in a desired direction (e.g., an extrusion movement where the tooth is moved in an occlusal or incisal direction) as the appliance is worn by the patient. A tooth movement device can include a spring-loaded device disposed in the appliance and configured to engage an attachment mounted on a surface of the patient's tooth. Rather than having a device or means for applying resilient force to a tooth that span multiple teeth or span between the opposing jaws as in prior approaches (e.g., elastic bands engaging hooks on brackets/attachment on opposing teeth/jaws), the tooth movement device according to the current invention is positioned adjacent (e.g., directly adjacent) to the tooth to which the movement force is being applied.

Spring-loaded tooth movement devices, disposed in either the appliance or an attachment to the tooth, can include various designs and components for delivery of a tooth movement force to the tooth. Spring-loaded devices will not be limited to spring assemblies per se, and can include both spring-containing assemblies and non-spring assemblies designed to apply a resilient or elastic force to a tooth, such as compression assemblies, cylinder/piston assemblies, elastic members, cantilevers, and the like. Thus, spring-loaded tooth movement devices allow application of a force to the tooth separate from or in addition to any elastic force that may be applied to the tooth by contact (e.g., direct contact of appliances and tooth surface) of an appliance cavity or wall itself, e.g., resilient force due to appliance tooth cavity geometry and elasticity as the appliances is worn by the patient.

Various tooth movements can be accomplished according to the present invention. In one embodiment, a desired tooth movement includes a tooth extrusion movement, and a tooth movement device includes an extrusion device. While exemplary embodiments are provided herein illustrating extrusion type tooth movements, various tooth movement can be accomplished and be selected, for example, based and design and/or positioning of a tooth movement device and/or tooth attachment. In addition to extrusion movements, forces applied to a tooth can be selected to elicit tooth intrusions, rotations, tipping, translation, as well as movements in one or more various directions including mesial, distal, buccal, lingual, incisal, gingival directions.

An appliance of the invention can include a relief with the tooth movement device at least partially disposed in the relief. The tooth movement device can be configured to engage (e.g., in a mesial-distal orientation/direction) opposing sides of the attachment mounted on the tooth. Engagement of the tooth movement device and attachment allows application of the desired force to the tooth as the appliances is worn by the patient. The mounted attachment can include inclined surfaces and the tooth movement device can be configured to engage the inclined surfaces on opposing sides of the attachment such that action on the tooth movement device against the inclined surfaces creates a force vector to elicit a tooth movement perpendicular to the direction of tooth movement device action. An appliance can include a single tooth movement device or a plurality thereof. For example, a plurality of tooth movement devices, disposed either in the appliance or a tooth attachment as described below (or both), can be used to engage a single tooth or a plurality of different teeth. In one embodiment, tooth movement devices can be utilized as described herein to engage opposing surfaces of a tooth (e.g., buccal side surface and lingual side surface), for example, and in some cases may deliver a more balanced net force to the target tooth.

Various attachments, including materials and designs, can be utilized according to the present invention to apply the selected extrusion force to a patients tooth. Attachments can include various materials, e.g., metal, glass, composite, plastic, etc. For example, attachments can be formed by application and in some cases curing of material (e.g., composite) on a tooth surface, with the material applied to the tooth surface using a template, such as a customized template. Customized templates can be produced, for example, using a model of the patient's teeth so the template substantially matches the teeth in an expected position/arrangement at the time of attachment positioning, with the template further including a space or relief for attachment material delivery/application to the patient's tooth. Attachment materials can further include various pre-formed or pre-fabricated components, such as attachment devices. Materials for attachment positioning, such as templates, attachment materials, etc, can optionally be provided to an orthodontic practitioner for attachment positioning.

Various designs or assemblies can be selected for application of a force as described herein. In one embodiment, a tooth movement device can include a spring clip coupled with the appliance. For example, a spring clip can be disposed on the appliance, with the spring clip including opposing spring arms or prongs configured to engage the mounted attachment when the appliance is worn by the patient. Suitable spring clips are not limited to any particular composition or design and can be selected from various metals, plastics, or other suitable spring-loaded materials for delivering the desired force to the mounted attachment. In another embodiment, a tooth movement includes an extrusion device and can include one or more spring-loaded contact assemblies, such as spring-loaded sliding contact element assemblies positioned to apply force to generally opposing sides of a mounted attachment. In one example, a spring-loaded sliding contact assembly can include a spring and sliding ball assembly.

The present invention includes systems for providing orthodontic treatment to a patient including a plurality of incremental tooth position adjustment appliances. A plurality of appliances can include a set or series of patient removable appliances for positioning a patient's teeth along a treatment path from an initial position, through one or more intermediate tooth arrangements, and toward a final or desired position or arrangement of the patient's teeth (e.g., prescribed or target arrangement). Thus, the plurality of appliances can include appliances for each of any number (e.g., two or more) of intermediate arrangements for positioning the patient's teeth from an initial position toward a final position. Each patient removable appliance can include teeth receiving, and cavities of successive appliances of the plurality can have different geometries shaped to receive and resiliently reposition teeth from one arrangement to a successive arrangement. A plurality of appliances of a system can include at least one appliance including a spring-loaded tooth movement device as described herein. A tooth movement device can be disposed in the appliance (e.g., appliance cavity) so as to engage an attachment mounted on a surface of the patient's tooth and apply a force to the tooth, which may elicit movement of the tooth, e.g., an extrusion movement in an occlusal or incisal direction.

In another embodiment, a system of the present invention can include an attachment assembly mountable on a surface of a tooth, with the attachment assembly including a spring-loaded tooth movement device (e.g., extrusion device). The tooth movement device is positioned adjacent to the tooth to which the movement force is being applied. For delivery of an aspect of orthodontic treatment, an orthodontic appliance designed to engage the attachment assembly will be provided. Similar to above, the appliance can include teeth receiving cavities with a cavity having a relief disposed therein and shaped to receive the spring-loaded device of the attachment assembly. As the appliance is worn by the patient, the attachment assembly with the device coupled with the appliance function to apply a force to the tooth. Various device, extrusion device designs and configurations will be available. In one embodiment, a tooth movement device such as an extrusion device of an attachment assembly can include a spring-loaded sliding contact element assembly (e.g., spring and sliding ball assembly) that engages a surface of a relief of the appliance and applies a force (e.g., extrusion force) to the tooth as the appliance is worn by the patient. Spring loaded sliding contact element assemblies can include various sliding contact elements, such as a sliding ball, semi-ball, probe, etc.

The present invention further includes methods for providing orthodontic treatment to a patient's teeth, for example, utilizing a device or system of the present invention. In one embodiment, a method includes mounting an attachment on a surface of a tooth of a patient, and providing a positioning appliance including a spring-loaded tooth movement device disposed in the appliance. In another embodiment, the attachment includes a spring-loaded tooth movement device/assembly, as described further herein. In such an embodiment, the attachment can be provided for mounting to a surface of the patient's tooth, and an appliance further provided that is customized or designed to receive the spring-loaded tooth movement device of the mounted attachment assembly and apply a force to the tooth as the appliances is worn by the patient.

Mounting an attachment can include bonding the attachment to the surface of the patient's tooth. Bonding and attachment positioning can be accomplished according to various techniques, including those commonly employed in orthodontics for mounting or bonding an attachment or object to a patient's tooth. In some instances, the step of mounting an attachment can include merely providing certain materials and/or instructions to an orthodontic practitioner and allowing the practitioner to accomplish the bonding or positioning of the attachment. For example, in one embodiment, a practitioner may be supplied with a template that facilitates attachment placement or bonding to the tooth. Templates can include certain customized templates configured to facilitate attachment bonding and positioning to correspond with a customized appliance that engages the mounted attachment as the appliance is worn by the patient. Providing a customized template can help ensure correct attachment positioning for more optimal delivery of treatment or use of an appliance or system of the present invention. For general discussion of certain techniques and methodologies that may find use in the present invention, including exemplary attachments, mounting/bonding methodologies, templates, etc., see patents and patent applications assigned to Align Technology, Inc., including U.S. Pat. Nos. 6,309,215; 6,830,450; and U.S. patent application Ser. No. 10/863,991.

Figure 1:
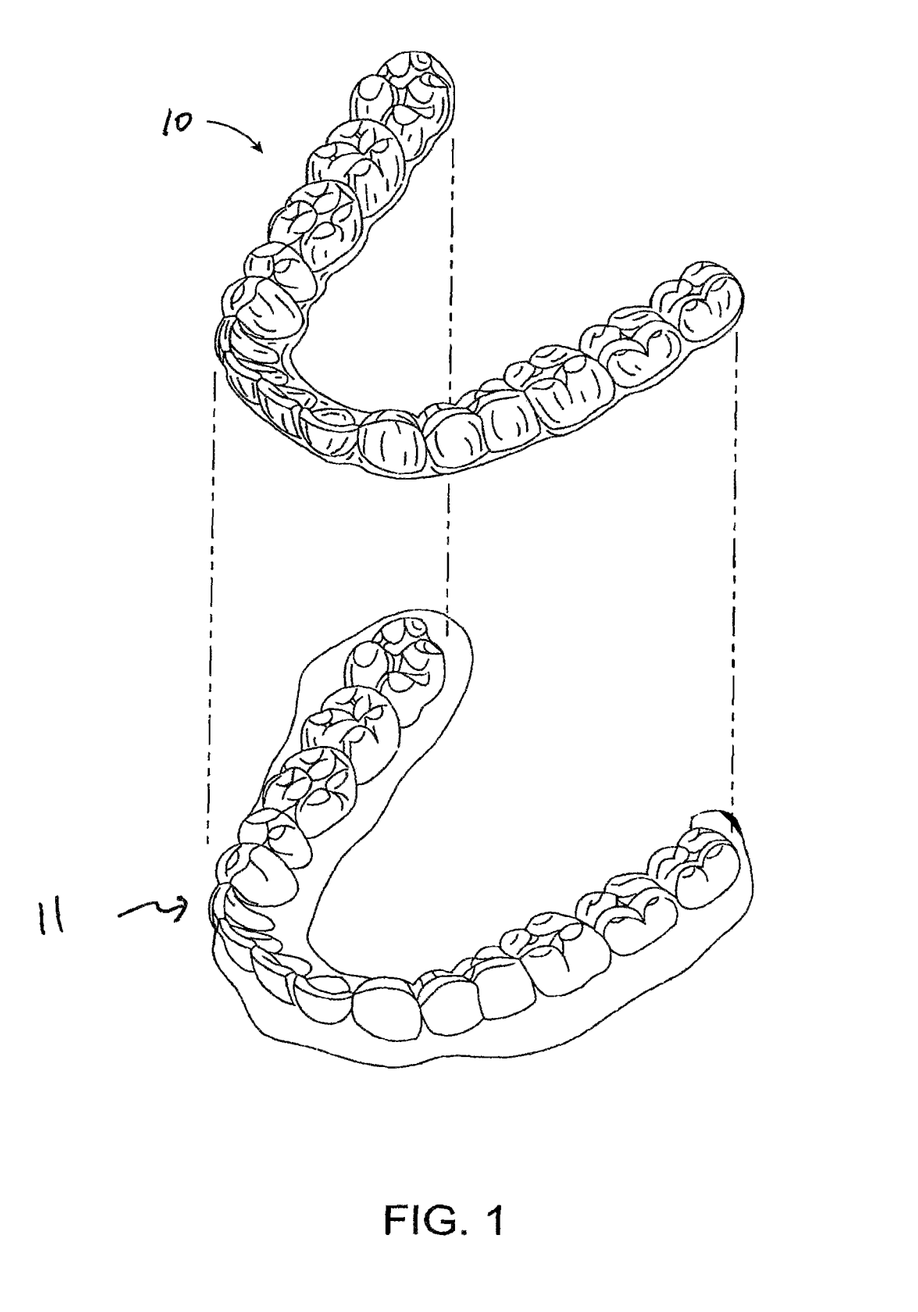
FIG. 1 illustrates a jaw together with an incremental positioning appliance according to an embodiment of the present invention.

FIG. 1 shows one adjustment appliance 10 which is worn by the patient in order to achieve an incremental repositioning of individual teeth in the jaw 11. The appliance can include a shell (e.g., polymeric shell) having teeth-receiving cavities that receive and resiliently reposition the teeth. In one embodiment, a polymeric appliance can be formed from a thin sheet of suitable elastomeric polymeric material, such as Tru-Train (e.g., 0.03 inch) thermal forming dental material (Tru-Train Plastics, Rochester, Minn.). An appliance can fit over all teeth present in an upper or lower jaw, or less than all of the teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth which are moved can also serve as a base or anchor for holding the appliance as it is worn by the patient. Typically, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "align.com"). Appliances according to the present invention are further designed to include aspects such that the appliance is configured to operate in conjunction with one or more tooth movement devices disposed in the appliance itself and/or in an attachment mounted to a surface of a patient's tooth, as described herein.

An appliance can be designed and/or provided as part of a set or plurality of appliances. In such an embodiment, each appliance may be configured so a tooth-receiving cavity has a geometry corresponding to an intermediate or final tooth arrangement intended for the appliance. The patient's teeth are progressively repositioned from their initial tooth arrangement to a final tooth arrangement by placing a series of incremental position adjustment appliances over the patient's teeth. The adjustment appliances can be generated all at the same stage or in sets or batches, e.g., at the beginning of a stage of the treatment, and the patient wears each appliance until the pressure of each appliance on the teeth can no longer be felt or has resulted in the maximum allowable tooth movement for that given stage. A plurality of different appliances (e.g., set) can be designed and even fabricated prior to the patient wearing any appliance of the plurality. After wearing an appliance for an appropriate period of time, the patient replaces the current appliance with the next appliance in the series until no more appliances remain. The appliances are generally not affixed to the teeth and the patient may place and replace the appliances at any time during the procedure (e.g., patient removable appliances). The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Figure 2:
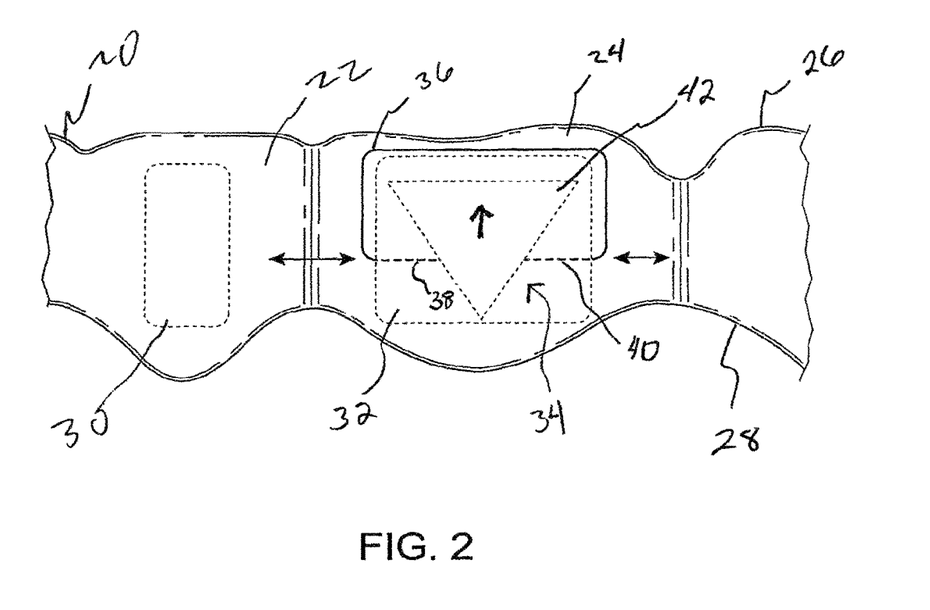
FIG. 2 illustrates a positioning appliance including a spring clip extrusion device according to an embodiment of the present invention.

FIG. 2 illustrates a side view of a positioning appliance including a spring clip extrusion device according to an embodiment of the present invention. The illustrated appliance 20 includes a shell appliance having tooth receiving cavities 22, 24, the appliance 20 having an incisal side 26 and a gingival side 28. Cavity 22 includes relief 30 formed by a protrusion in appliance material, the relief 30 shaped to receive an attachment positioned on a corresponding tooth received in cavity 22. Cavity 24 includes a relief 32 formed at least partially by a protrusion appliance material of cavity 24, the cavity 24 further including extrusion device 34 coupled with the relief 32. The extrusion device 34 includes a spring-loaded clip 36 coupled with the appliance 20. The clip 36 as shown includes a length of material having opposing ends or prongs 38, 40 with the clip coupled with the appliance such that the prongs 38, 40 extend through the relief 32 and to the interior of the relief 32 or tooth receiving cavity 24. A portion of the clip 36 between the prongs 38, 40 can extend about an exterior portion of the relief 32. The clip 36 may optionally be held in place with a securing means such as an adhesive or anchoring mechanism. In use, prongs 38, 40 of the clip interface 36 with an attachment 42 that will be mounted or bonded to a tooth received in the cavity 24. Spring action of the clip 36 as positioned in the appliance 20 is illustrated by bi-directional arrows oriented in a generally lateral direction (e.g., mesial-distal direction). As shown, the attachment 42 will typically have inclined surfaces such that action of the spring prongs against opposing inclined surfaces of the attachment 42 creates a vertical vector (illustrated by the upward pointing arrow) to elicit a movement perpendicular to the direction of the spring arm activation. Thus, engaging of the clip 36 and tooth attachment 42 and action of the clip prongs 38, 40 against the inclined surfaces of the tooth attachment 42, generates an extrusion force on the tooth and can move the tooth in an incisal or occlusal direction.

Figure 3:
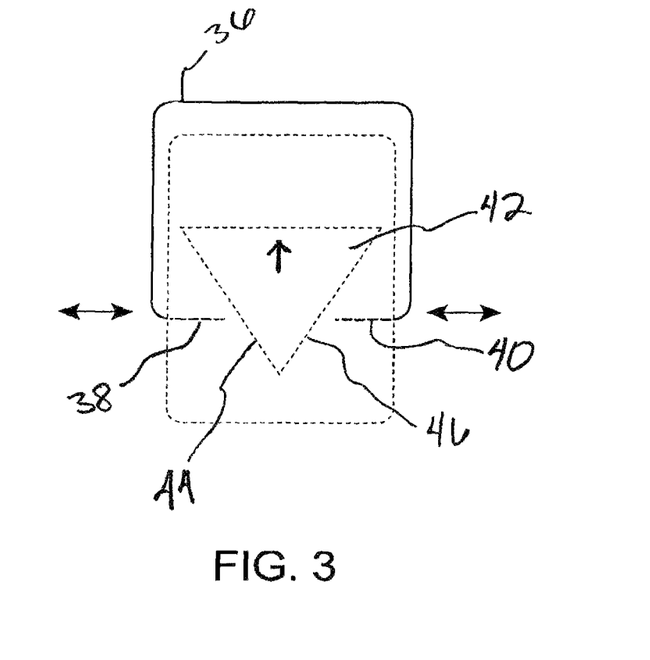
FIG. 3 illustrates a spring clip and shaped tooth attachment for generating an extrusion force on a tooth, according to an embodiment of the present invention.

FIG. 3 shows a conceptual diagram of a spring clip and shaped tooth attachment for generating an extrusion force on a tooth, as illustrated in FIG. 2. The spring clip includes prongs 38, 40 oriented to engage a tooth attachment 42 laterally or in a generally mesial-distal direction. Movement of the prongs 38, 40 of the spring-loaded clip 36 are illustrated by bi-directional arrows. A force can be applied to create space or distance between ends of the prongs 38, 40, e.g., for positioning of the clip 36 to engage the attachment 42 for desired use and application of extrusion force to the teeth. Removal of the spacing force allows the action of the spring-loaded clip 36 to bring the prongs 38, 40 into contact with inclined surfaces 44, 46 of the attachment, respectively. Action of the spring prongs 38, 40 against opposing inclined surfaces 44, 46 of the attachment creates an extrusion force to the tooth by creation of a vertical vector (upward pointing arrow) as the attachment 42 is sort of squeezed out from the opposing prongs 38, 40, thereby eliciting a movement perpendicular to the direction of the spring arm/prong activation.

Figure 4A:
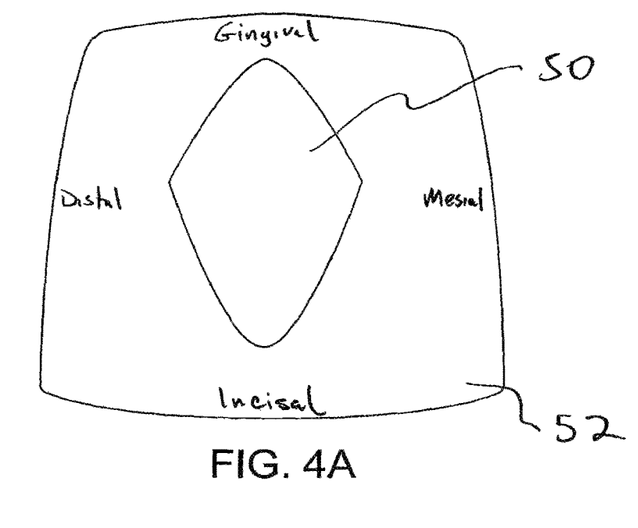
FIGS. 4A through 4C illustrate a shaped tooth attachment and an extrusion device for applying an extrusion force to a tooth, according to another embodiment of the present invention.
Figure 4B:
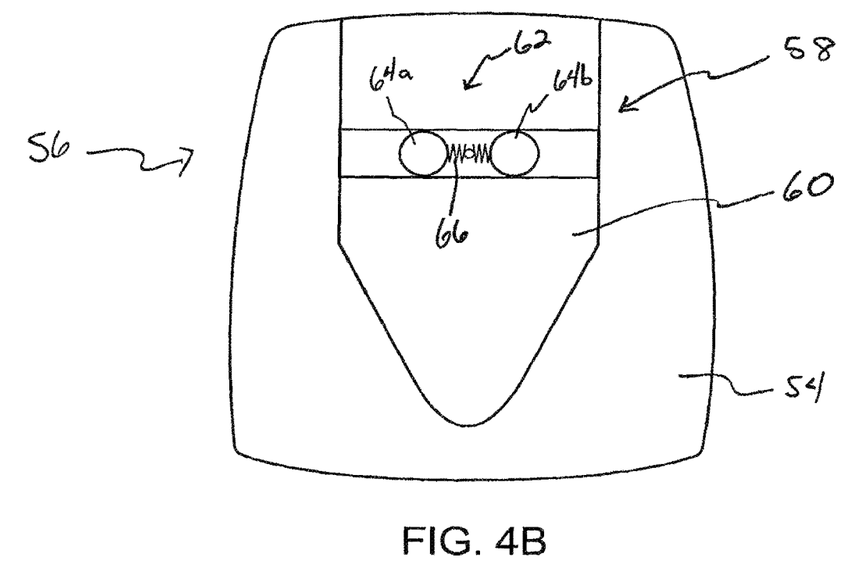
Figure 4C:
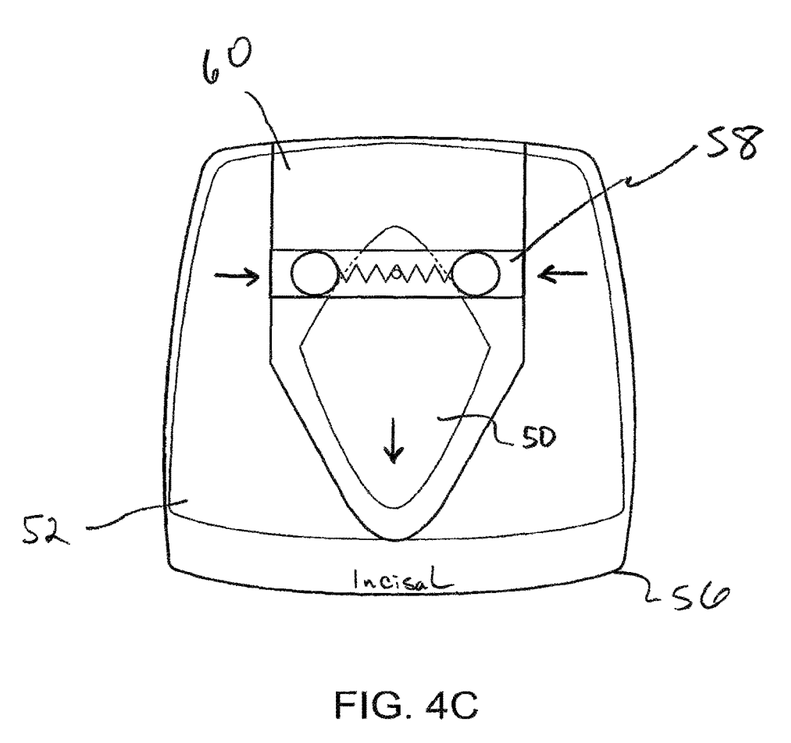

FIGS. 4A through 4C illustrate a shaped tooth attachment and an extrusion device for applying an extrusion force to a tooth, according to another embodiment of the present invention. FIG. 4A illustrates a tooth attachment 50 mounted on a surface of a patient's tooth 52. As illustrated, the attachment 50 includes inclined surfaces that, during use of an appliance, engage an extrusion device of an appliance. The attachment 50 will typically include a triangular or diamond shape, with opposed inclined surfaces slanted or angled in a mesial or distal direction/orientation. FIG. 4B illustrates a tooth receiving cavity 54 of an appliance 56 including an extrusion device 58. The appliance cavity 54 includes a relief 60 with an extrusion device 58 disposed therein. The extrusion device 58 includes spring-loaded sliding contact assembly 62. In the illustrated embodiment, a contact assembly can include a sliding device, such as a sliding ball 64a, 64b, with opposing sliding devices attached to each other about elastics/springs 66 and embedded into the appliance 56. In another embodiment, rather than an elastic/spring attached to opposing sliding devices so as to pull the devices toward each other, sliding devices can each separately include a spring coupled to the sliding device so as to independently push sliding devices toward each other and in the desired direction (not shown). FIG. 4C illustrates the patient's tooth 52 with the mounted attachment 50 positioned in the tooth receiving cavity 54 of the appliance 56 having the extrusion device 58. With the appliance 56 positioned in place, the extrusion device 58 engages the attachment 50 and applies a extrusion force to the tooth 52. A portion of the attachment 50 is disposed between the sliding devices 64a, 64b, of the extrusion device. Elastics/spring-loaded action of the sliding devices 64a, 64b, brings the devices into contact with the inclined surfaces of the attachment 50, applying a lateral force to the attachment 50 as illustrated by force vector arrows. Action of the sliding devices 64a, 64b, of the extrusion device 58 against the inclined surfaces of the attachment 50 creates a vertical force vector for tooth extrusion, as illustrated by the downward pointing arrow in FIG. 4C. The extrusion force can elicit tooth movement in an incisal direction and/or perpendicular to the direction of sliding device action on the attachment 50. As illustrated in FIG. 4C, the relief 60 can be shaped to include a space to accompany movement of the attachment 50 as the tooth 52 is moved in the desired direction without obstruction by a surface or portion of the appliance 56.

Figure 5:
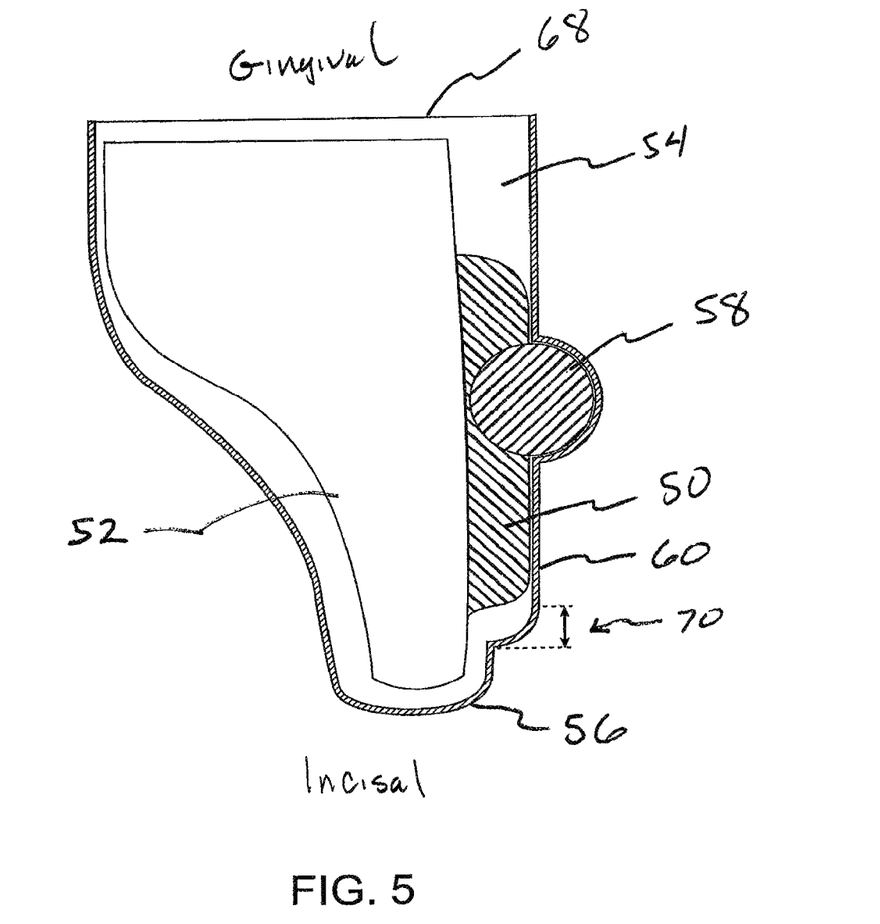
FIG. 5 illustrates a cross-sectional side view of an appliance cavity having an extrusion device engaging an attachment, according to an embodiment of the present invention.

FIG. 5 illustrates a cross-sectional side view of an appliance as illustrated in FIGS. 4A through 4C, showing an appliance cavity 54 having an extrusion device 58 engaging an attachment 50. The appliance cavity 54 is open on a gingival side 68 for positioning of the appliance 56 over the tooth 52, with the tooth 52 disposed in the tooth receiving cavity 54 during use. The attachment 50 is mounted on a surface of the tooth 52 and received in the relief 60 so as to engage the attachment 50 with the extrusion device 58 as illustrated above. The relief 60 includes a space 70 to allow movement of the attachment 50 during extrusion. The tooth receiving cavity 54 can similarly be shaped to accommodate tooth movement. The sliding device of the extrusion device 58 engages the mounted attachment 50 and applies the desired force, which can elicit a desired tooth movement.

In another embodiment, a system of the present invention can include a tooth attachment having a spring-loaded extrusion device. The attachment can include a spring-loaded sliding contact assembly that may allow application of force to a patient's tooth in the desired direction when the attachment is used in conjunction with a corresponding tooth positioning appliance. A tooth positioning appliance will have teeth receiving cavities shaped to receive and the patient's teeth and apply the desired resilient positioning force. The appliance will have a cavity designed to receive a tooth having the attachment with the extrusion device, with the cavity having a relief disposed therein and shaped to receive the spring-loaded device of the mounted attachment.

Engagement of the appliance and the tooth mounted attachment as the appliances is worn by the patient allows application of an extrusion force to the tooth. The extrusion device of the attachment can include, e.g., a spring-loaded sliding contact assembly including a spring and sliding ball assembly. An attachment can be in form of a sort of box, with the box including an opening on a side. The opening can be designed to allow a partial extrusion of the contact element (e.g., ball, rounded or hemispheric shaped element, etc.) attached to a spring positioned inside the attachment box. During use, positioning of the appliance on the tooth having the attachment mounted thereon will push the contact element toward the inside of the box. As the appliance is worn by the patient, the spring-loaded contact element will contact a portion of the appliance and exert a force to move the tooth in the desired direction. The appliance will be shaped to accommodate movement of the tooth and attachment within the cavity.

Figure 6A:
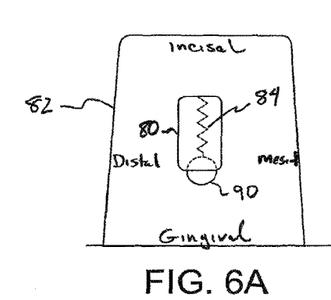
FIGS. 6A through 6F shows a tooth extrusion system of the present invention including a tooth attachment having a spring-loaded extrusion device, according to another embodiment of the present invention.
Figure 6B:
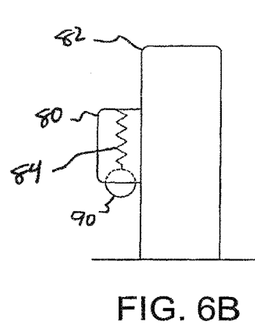
Figure 6C:
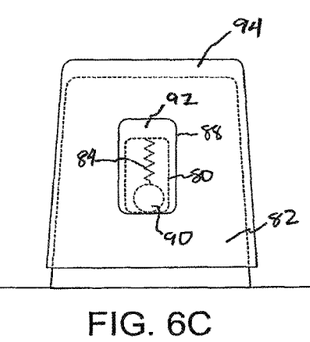
Figure 6D:
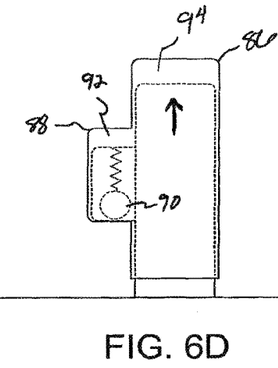
Figure 6E:
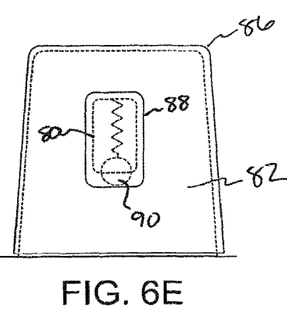
Figure 6F:
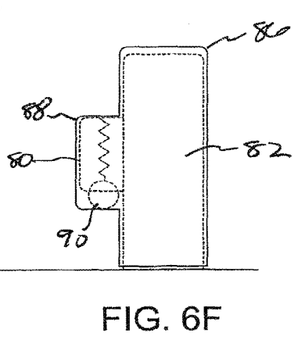

FIGS. 6A through 6F shows conceptual diagrams of a tooth extrusion system of the present invention including a tooth attachment having a spring-loaded extrusion device. FIGS. 6A and 6B respectively illustrate a front view and a side view of an attachment 80 mounted on a tooth 82, with the attachment 80 including an extrusion device 84 with a spring-loaded contact element assembly 90 with a sliding ball and spring. The tooth 82 with attachment 80 is positioned in a tooth receiving cavity of an appliance 86 (FIGS. 6C and 6D). With the appliance 86 in position, the attachment 80 is disposed in a relief 88 in the cavity. Positioning of the appliance 86 compresses the spring as the sliding contact element 90 is pushed inside the attachment 80. The force resulting from the compressed spring presses the sliding contact element 90 against a surface of the appliance and creates a force on the tooth in a direction opposite of action of the contact element 90 against the appliance surface (see force arrow in FIG. 6D indicating force direction). The appliance cavity and the relief 88 will be shaped to include spaces 92, 94 to accommodate movement of the tooth and attachment in the desired direction. FIGS. 6E and 6F illustrate tooth movement following application of the appliance 86 to the patient's tooth 82. After a period of time, the contact element 90 extends out the opening in the attachment 80 as the spring de-compresses, and the tooth moves in a selected direction to occupy space 94 in a portion of the cavity (e.g., incisal portion). Likewise, the attachment 80 is moved into the previously unoccupied space 92.

The present invention can make use of various computer or non-computer implemented techniques for designing appliances as described, as well as implementing various embodiments of the methods described herein. For example, a computer implemented method in one embodiment includes establishing an initial position of a tooth, determining a target position of the tooth in a treatment plan, calculating a movement vector associated with the tooth movement from the initial position to the target position, determining a plurality of appliance components corresponding to the movement vector, and determining a corresponding one or more positions/profiles of a respective one or more elements or aspects of an orthodontic appliance. The extrusion devices may be configured to apply a predetermined force to the patient's tooth/teeth in accordance with the desired tooth movement.

A patient's orthodontic treatment utilizing devices and methods described herein can be accomplished according to a treatment plan. Exemplary methods treatment plan design, as well as appliance design and fabrication are described further below. Typically, appliance and/or treatment plan can optionally, though not necessarily, be accomplished using various computer based applications. It will be recognized that appliance design and fabrication is not limited to any particular method and can include various computer and non-computer based methodologies.

Treatment planning, according to one embodiment of the present invention, is described. Patient data can be collected and analyzed, and specific treatment steps specified and/or prescribed. In one embodiment, a treatment plan can be generated and proposed for a dental practitioner to review. The dental practitioner can accept or request modifications to the treatment plan. Once the treatment plan is approved, manufacturing of appliance(s) can begin. Generating and/or analyzing treatment plans, as discussed herein, can include, for example, use of 3-dimensional orthodontic treatment planning tools such as Treat® from Align Technology, Inc. or other software available from eModels and OrthoCAD, among others. These technologies allow the clinician to use the actual patient's dentition as a starting point for customizing the treatment plan. The Treat® technology uses a patient-specific digital model to plot a treatment plan, and then use a scan of the achieved or actual treatment outcome to assess the degree of success of the outcome as compared to the original digital treatment plan as discussed in U.S. patent application Ser. No. 10/640,439, filed Aug. 21, 2003 and U.S. patent application Ser. No. 10/225,889 filed Aug. 22, 2002.

A system or apparatus for providing a method of the present invention, such as modeling a dental appliance, in one embodiment can include a data storage unit, and a processing unit coupled to the data storage unit and configured to determine an initial position of a tooth, determine a target position of the tooth in a treatment plan, calculate a movement vector associated with the tooth movement from the initial position to the target position, determine a plurality of components corresponding to the movement vector, and determine a profile and/or positioning of corresponding one or more elements/aspects of an appliance.

The data processing aspects of the invention can be implemented in digital electronic circuitry, or in computer hardware, firmware, software, or in combinations of them. Data processing apparatus of the invention can be implemented in a computer program product tangibly embodied in a machine-readable storage device for execution by a programmable processor; and data processing method steps of the invention can be performed by a programmable processor executing a program of instructions to perform functions of the invention by operating on input data and generating output. The data processing aspects of the invention can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits). Computer-based systems can include network based systems or may be coupled to a network.

To provide for interaction with a user, the invention can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse. The computer system can be programmed to provide a graphical user interface through which computer programs interact with users. The computer system can be programmed to provide a virtual reality, three-dimensional display interface.

It is understood that the examples and embodiments described herein are for illustrative purposes and that various modifications or changes in light thereof may be suggested to persons skilled in the art and are included within the spirit and purview of this application and the scope of the appended claims. Numerous different combinations are possible, and such combinations are considered to be part of the present invention.

What is claimed is:

1. An orthodontic appliance for positioning a patient's teeth, the appliance comprising:
    a shell comprising a plurality of cavities shaped to receive and apply a resilient positioning force to the patient's teeth; and
    a spring-loaded tooth movement device at least partially disposed in a cavity of the shell, wherein the spring-loaded tooth movement device is arranged so as to engage an attachment mounted on a surface of a tooth in order to produce vertical movement of the tooth relative to the cavity, the vertical movement of the tooth relative to the cavity being greater than buccal or lingual movement of the tooth relative to the cavity.

2. The appliance of claim 1, wherein the vertical movement comprises an extrusion movement towards an incisal or occlusal side of the cavity.

3. The appliance of claim 2, wherein the tooth movement comprises an extrusion device configured to engage opposing sides of the attachment so as to apply an extrusion force to the tooth when the appliance is worn by the patient.

4. The appliance of claim 3, wherein the extrusion device is configured to engage inclined surfaces on the opposing sides of the attachment so as to apply the extrusion force to the tooth.

5. The appliance of claim 3, wherein the extrusion device is configured to engage the attachment by action along a mesial-distal direction on the opposing sides of the attachment.

6. The appliance of claim 3, wherein the extrusion device comprises a spring clip disposed in the cavity, the spring clip comprising opposing prongs configured to engage the attachment when the appliance is worn by the patient.

7. The appliance of claim 3, wherein the extrusion device comprises opposing spring-loaded sliding contact element assemblies that engage the attachment when the appliance is worn by the patient.

8. The appliance of claim 1, wherein the cavity comprises a space shaped to accommodate movement of the attachment relative to the cavity.

9. The appliance of claim 1, further comprising a plurality of spring-loaded tooth movement devices.

10. A method for positioning a patient's teeth, the method comprising:
    providing a removable orthodontic tooth positioning appliance comprising:
        a shell comprising a plurality of cavities shaped to receive and apply a resilient positioning force to the patient's teeth,
        a spring-loaded tooth movement device at least partially disposed in a cavity of the shell, wherein the spring-loaded tooth movement device is arranged so as to engage an attachment mounted on a surface of a tooth in order to produce vertical movement of the tooth relative to the cavity, the vertical movement of the tooth relative to the cavity being greater than buccal or lingual movement of the tooth relative to the cavity; and
    placing the removable orthodontic tooth positioning appliance on the teeth of a patient.

11. The method of claim 10, wherein the vertical movement comprises an extrusion movement toward an incisal or occlusal side of the cavity.

12. The method of claim 11, wherein the tooth movement device comprises an extrusion device configured to engage opposing sides of the attachment so as to apply an extrusion force to the tooth when the appliance is worn by the patient.

13. The method of claim 12, wherein the extrusion device comprises a spring clip disposed in the cavity, the spring clip comprising opposing prongs configured to engage the attachment when the appliance is worn by the patient.

14. The method of claim 10, further comprising mounting the attachment on the surface of the tooth.

15. The appliance of claim 10, wherein the cavity comprises a space shaped to accommodate movement of the attachment relative to the cavity.

16. A system for positioning a patient's teeth, the system comprising:
    a plurality of removable orthodontic tooth positioning appliances each comprising a shell comprising a plurality of cavities shaped to receive and apply a resilient positioning force to the patient's teeth,
    wherein at least one removable orthodontic tooth positioning appliance of the plurality of removable orthodontic tooth positioning appliances comprises a spring-loaded tooth movement device at least partially disposed in a cavity of the shell, and wherein the spring-loaded tooth movement device is arranged so as to engage an attachment mounted on a surface of a tooth in order to produce vertical movement of the tooth relative to the cavity, the vertical movement of the tooth relative to the cavity being greater than buccal or lingual movement of the tooth relative to the cavity.

17. The system of claim 16, wherein the vertical movement comprises an extrusion movement toward an incisal or occlusal side of the cavity.

18. The system of claim 17, wherein the tooth movement comprises an extrusion device configured to engage opposing sides of the attachment so as to apply an extrusion force to the tooth when the at least one removable tooth positioning appliance is worn by the patient.

19. The system of claim 16, wherein the cavity comprises a space shaped to accommodate movement of the attachment relative to the cavity.

20. The system of claim 16, wherein the spring-loaded tooth movement device is disposed in the cavity so as to engage the attachment and apply a force to the tooth separate from any force applied to the tooth by one or more surfaces of the cavity.

* * * * *